United States Patent [19]
Lin

[11] Patent Number: 4,806,678
[45] Date of Patent: Feb. 21, 1989

[54] PROCESS FOR THE HYDROFORMYLATION OF ALLYLIC ESTERS USING A COBALT CATALYST

[75] Inventor: Jiang-Jen Lin, Round Rock, Tex.

[73] Assignee: Texaco Inc., White Plains, N.Y.

[21] Appl. No.: 541,619

[22] Filed: Oct. 13, 1983

[51] Int. Cl.$^4$ .................. C07C 67/38; C07C 69/67
[52] U.S. Cl. ............................. 560/266; 562/607; 568/451; 568/455
[58] Field of Search .................................. 560/266

[56] References Cited

U.S. PATENT DOCUMENTS 3,231,621 1/1966 Slaugh ............................. 560/266
3,725,305 4/1973 Wilkinson ........................ 562/519

Primary Examiner—Vivian Garner
Attorney, Agent, or Firm—Jack H. Park; Kenneth R. Priem; Cynthia L. Kendrick

[57] ABSTRACT

A process is disclosed for preparing compounds such as 4-acetoxybutyraldehyde which comprises contacting reactants such as allyl acetates with a cobalt carbonyl catalyst in the presence of various novel promoters. The promoters are selected from the group consisting of triphenyl germane, tetraphenyl germane, phenyl sulfide, succinonitrile and 2,2'-dipyridyl. The reaction is preferably conducted in the presence of a ketone solvent.

5 Claims, No Drawings

PROCESS FOR THE HYDROFORMYLATION OF ALLYLIC ESTERS USING A COBALT CATALYST

BACKGOUND OF THE INVENTION

1. Field of the Invention

This invention is related to the addition of hydrogen and carbon monoxide to allylic ester compounds to obtain 4-acyloxybutyraldehydes in the presence of a cobalt-containing catalyst and is more particularly related to such an addition conducted in the presence of germanium, sulfide, nitrile and amine promoters.

2. Description of Related Processes in the Field

The compound 4-acetoxybutyraldehyde is an important intermediate for producing 1,4-butanediol and γ-butyrolactone. Whether the former or latter is produced depends on whether the intermediate 4-acetoxybutyraldehyde is subsequently subjected to reduction or oxidation, respectively.

In U.S. Pat. No. 4,039,592 Smith discloses a process for the production of butanediol which comprises (a) reacting propylene, oxygen and acetic acid in the presence of a catalyst comprising a Group VIII noble metal or its salt or its oxides or mixtures thereof at an elevated temperature to yield allyl acetate; (b) hydroformylating the allyl acetate under hydroformylating conditions to produce a mixture of isomeric acetoxybutyraldehydes; (c) hydrogenating the mixture of isomeric acetoxybutyraldehydes under hydrogenating conditions to produce a mixture comprising the acetic esters of the corresponding butanediols; (d) de-esterifying the mixture of the acetate esters of the butanediols under deesterification conditions to produce the butanediols and acetic acid; and (e) isolating the acetic acid from the butanediols in a form suitable for use in (a). A different catalyst is used at each of several steps and a support material is required. The hydroformylation step proceeds at a high pressure with cobalt-containing catalyst.

In U.S. Pat. No. 4,035,408, Smith discloses a process of hydroformylating allyl acetate, or a mixture containing same, in the presence of a cobalt hydroformylation catalyst to produce a mixture comprising 4-acetoxybutyraldehyde as the predominant product along with its two isomers, 2-acetoxybutyraldehyde and 3-acetoxy-2-methyl-propionaldehyde. At least some of the main product is separated from the mixture containing its two isomers, and the mixture containing the two isomers is dehydroformylated, at a temperature in the range of 120°–250° C., in a non-oxidizing atmosphere in the presence of a catalyst selected from the group consisting of a Group VIII noble metal and mixtures thereof on an essentially neutral support to produce feedstock which is recycled to the hydroformylation step.

U.S. Pat. No. 3,980,670 discloses a process for manufacturing methacrylic acid and butyrolactone by hydroformylation of allyl esters of lower carboxylic acids in the presence of rhodium catalysts followed by oxidation of the resulting formyl compounds with molecular oxygen to produce 4-acetoxy-n-butyric acid as the major product. See also German Offen. No. 2,106,243 to BASF.

In the inventions discussed above, using cobalt or rhodium catalysts, isomeric co-products, accompanied with 4-acetoxybutyraldehyde, are usually produced. In some cases, an additional step is required to recycle the isomeric aldehyde products.

Various aspects of the General Electric cobalt catalyzed hydroformylation process using allyl acetate at 3,000 psi and 180° C. are outlined in West German Offenlegungsschrifts Nos. 2,425,844; 2,425,653; 2,425,843; 2,425,878; 2,425,761 and 2,425,845. General Electric has also found that 4-butyrolactone can be made from reacting 4-acetoxybutanoic acid in the presence of an acidic cyclization catalyst such as nitric acid, phosphoric acid, sufuric acid, etc. according to U.S. Pat. No. 3,868,370.

U.S. Pat. No. 4,209,467 assigned to Daicel, Ltd. teaches a low pressure hydroformylation process in which the catalyst is a reaction product of a cobalt carbonyl compound with a nitrogen-containing heterocyclic compound having an enolic hydroxyl group on the carbon atom adjacent to the ring-forming nitrogen atom, such as 2-hydroxypyridine. Ordinarily, the pressures employed therein are in the neighborhood of 30 atmospheres. Unsaturated compounds taught as suitable for this hydroformylation process include hydrocarbons such as ethylene, propylene, butadiene, etc. and compounds such as allyl alcohol, allyl acetate, etc.

Finally, a process for the production of predominantly linear and alpha-branched acetals by reacting a $C_3$ or higher alpha or internal olefin, carbon monoxide, hydrogen and a $C_1$–$C_5$ alkanol in the presence of a cobalt catalyst is revealed in U.S. Pat. No. 4,209,643. The improvement is that a promoter is present which is a quaternary ammonium salt such as N-benzyl,N,N,N-trimethylammonium methoxide. The preferred cobalt catalyst is dicobalt octacarbonyl.

U.S. Pat. No. 3,931,332 teaches that cobalt carbonyl catalysts can be stabilized for hydroformylation reactions by the presence of minor amounts of 2,2'-bipyridine, alkyl-substituted 2,2'-bipyridines, N-alkyl-substituted alkylene diamines and mixtures thereof.

U.S. Pat. No. 4,153,795 disclosed a hydroformylation catalyst which comprises (a) a cobalt carbonyl component and (b) at least one component selected from the group consisting of 3-pyridylpropionic acid esters of aliphatic polyhydric alcohols, 3-pyridylpropionic acid esters of aliphatic pyridyl alcohols and dipyridyl ethers. The catalysts promote hydroformylation of olefins at low temperature and pressure.

In Bull. Chem. Soc. Jpn. 53 214–218 (1980), Murata reported that complexes prepared in situ from $Co_2(CO)_8$ and some di(tertiary-phosphine)s are more active catalysts for the homogeneous hydroformylation of methyl acrylate than $CO_2(CO)_8$.

There is then a need in the art for producing 4-acetoxybutyraldehyde selectively, in high yield without production of isomeric co-products and using relatively mild operating conditions.

It is the primary object of the present invention to provide a process for the preparation of 4-acetoxybutyraldehyde selectively where high yield can be attained without the presence of isomerized co-products as found in other processes. Other objects include being able to conduct the reaction under low pressures (less than 1,000 psi). Conducting the reaction under reasonable reactions rates with a stable catalyst using a novel promoter is also an objective.

Other objects of the present invention will be apparent from the detailed description given hereinafter.

SUMMARY OF THE INVENTION

The invention concerns a process for preparing 4-acyloxybutyraldehydes which comprises hydroformylating allylic esters by reaction with carbon monoxide and hydrogen (synthesis gas) in the presence of a cobalt-containing catalyst and a promoter selected from the group consisting of triphenyl germane, tetraphenyl germane, phenyl sulfide, succinonitrile and 2,2'-dipyridyl in a ketone or ether solvent.

DESCRIPTION OF THE PREFERRED EMBODIMENTS

In general, the components of the hydroformylation reaction mixture, including the inert solvent, allylically unsaturated compound and cobalt catalyst and promoter may be added in any sequence as long as good agitation is employed to provide a good dispersion or a homogeneous reaction mixture. For example, the following represent some variations insofar as the addition of catalyst components, inert solvent and allyl ester addition that can be made without departing from the inventive process. These modifications include 1. The catalyst may be preformed and added to the reaction solvent prior to addition of the allyl ester and other inert solvent components.

2. Alternatively, to minimize stability problems with the catalyst, the catalyst is formed in situ, usually by mixing the inert solvent and allyl ester, followed by the addition of the catalyst components to form the reaction mixture.

3. After using either variation 1 or 2, the deoxygenated catalyst-containing reaction mixture is pressurized with CO and hydrogen and heated until the aldehyde product is formed.

A cobalt catalyst is used in the present invention. Any cobalt-containing compound capable of forming a cobalt carbonyl under the reaction conditions can be used. Dicobalt octacarbonyl is the most preferred cobalt compound.

The promoters suitable for use with the cobalt-containing catalysts of this invention may generally be described as germanium, sulfide, nitrile or amine compounds. The functions of the promoters include complexing and activating the cobalt carbonyl catalyst, allowing mild operating conditions, stabilizing the catalyst system by allowing the catalyst to remain in solution and controlling the product selectivity. It is especially preferred that the promoter be selected from the group consisting of triphenyl germane, tetraphenyl germane, phenyl sulfide, succinonitrile and 2,2'-dipyridyl. The most preferred promoters are tetraphenyl germane, triphenyl phenyl sulfide. These promoters increase the selectivity to 4-acetoxybutyraldehyde, a 1,4-butanediol precursor. The production of other by-products of the reaction, 2-methyl-3-acetoxypropanal, methacrolein, isobutyraldehyde and acetic acid, are suppressed, although all but acetic acid are used in methyl methacrylate synthesis.

The promoter is preferably present in a mole ratio of promoter/catalyst of between 0.1:1.0 to 2.0:1.0, and higher, if desired.

Suitable allylic ester substrates which may be employed in the instant invention for generating 4-acyloxybutyraldehydes are those allylic esters of the lower carboxylic acids, as illustrated by the following structure

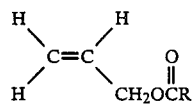

wherein R is selected from the group consisting of hydrogen and an alkyl radical containing 1 to 6 carbon atoms. The $CH_2$ methylene group between the allyl and ester functional groups may be a larger alkylene group, such as from $C_2$ to $C_8$. The process of this invention would certainly apply thereto although a 1,4-butanediol precursor would not be formed, of course. The preferred allylic ester substrate is allyl acetate.

The temperature range which can be employed for hydroformylation is a variable which is dependent upon experimental factors including the particular allylically unsaturated compound employed, the total pressure, the mole ratio of hydrogen and carbon monoxide used, the concentrations of reactants and catalyst, among other things. Using allyl acetate as the substrate and dicobalt octacarbonyl as a representative catalyst, an operable range is from about 25° C. to 125° C. or more when superatmospheric pressures of greater than 100 psig are employed. A narrower range of 80° C. to 120° C. represents the preferred temperature range when the aforementioned allyl acetate is hydroformylated.

The pressure range which can be employed for hydroformylation is a variable which is also dependent on the factors mentioned above. Using dicobalt octacarbonyl as a representative catalyst and allyl acetate as the substrate, an operable pressure range is from about 100 to 5,000 psig or more, with a mole ratio of $H_2/CO$ being 1:1 when a temperature range of from about 25° C. to 125° C. is employed. A narrower range of from 500 to 1,000 psig represents the preferred pressure range when the narrower temperature range of 80° C. to 120° C. is employed.

The $H_2/CO$ mole ratio may be varied over a range of from 30:1 to 1:30 when suitable temperatures and pressures are employed. A preferred narrower range is from 2:1 to 1:2 of hydrogen/carbon monoxide.

As previously indicated in the analogous discussion on temperatures and pressures required in the reaction, experimental variables are important in arriving at reaction times. Generally, substantial conversions (80% or higher) of the allyl acetate to 4-acetoxybutyraldehyde can almost always be accomplished within 18 hours, with 2 to 6 hours representing the more usual reaction time interval.

Experimental work indicates that an initial molar ratio of 10 moles to 10,000 moles of allyl ester per mole of cobalt-containing catalyst complex can be employed in most instances where said allyl ester is allyl acetate. The minimal ratio of 0.0001 moles of catalyst per mole of allyl acetate is herein referred to as a "catalytic ratio" or "catalytic amount". Much higher ratioes (i.e., 25 moles of substrate per mole of cobalt catalyst complex) are not harmful but are economically unattractive. For this reason the favored mole ratio ranges from 50 to 500 moles of allyl acetate per mole of cobalt catalyst complex.

The novel hydroformylation is run most conveniently in the presence of an inert diluent. Preferably, the solvent is polar. A variety of solvents can be used including ketones such as acetone, 2-undecanone, methyl ethyl ketone, methyl isobutyl ketone (MIBK), acetophenone, diethyl ketone, methyl propyl ketone and cyclohexanone and ethers such as phenyl ether.

Allyl acetate hydroformylation products, including 4-acetoxybutyraldehyde, may be isolated by the usual chemical or physical techniques, such as distillation, solvent extraction, chromatography, etc. Identification is by nuclear magnetic resonance and/or gas-liquid chromatography.

Conversion as defined herein represents the extent of conversion of the reacting allyl acetate to other products. Conversion is expressed as a percentile and is calculated by dividing the amount of allyl acetate consumed during hydroformylation by the amount of acetate originally charged and multiplying the quotient by 100.

Yield, as defined herein, represents the efficiency in catalyzing the desired hydroformylation reaction relative to other undesired reactions. In this instance hydroformylation to 4-acetoxybutyraldehyde is the desired conversion. Yield is expressed as a percentile and is calculated by determining the amount of 4-acetoxybutyraldehyde product formed, divided by the amount of allyl acetate charged and multiplying the quotient obtained by 100.

Selectivity, as defined herein, is the efficiency in catalyzing a desired hydroformylation reaction relative to the other undesired conversion. Selectivity is expressed as a percentile and is calculated by determining the amount of 4-acetoxybutyraldehyde product formed, divided by the total amount of $C_3$ plus $C_4$ products formed and multiplying the quotient obtained by 100.

Having described the inventive process in general terms, the following examples are submitted to supply specific and illustrative embodiments.

EXAMPLE 1

To a magnedrive stirred reactor (300 ml) was charged dicobalt octacarbonyl (0.34 g, 1 mm), phenyl sulfide (0.098 g, 0.5 mm), allyl acetate (10 g) and 2-undecanone (35.0 g). The reactor was flushed with synthesis gas and pressured to 100 psi with synthesis gas ($CO/H_2$ molar ratio=1:2), then heated to 90° C. with stirring. Then the pressure was increased to 800 psi and these conditions maintained with additional synthesis gas for 6 hours. The reaction was terminated, the reactor was allowed to cool to room temperature and a brown product solution was obtained. The gas-liquid chromatographic and nuclear magnetic resonance analyses gave the following product distribution.

|  | % Selectivity |
|---|---|
| 4-acetoxybutyraldehyde | 57 |
| 2-methyl-3-acetoxypropanal | 11 |
| Methacrolein | 7 |
| Isobutyraldehyde | 7 |
| Acetic acid | 7 |

The conversion of allyl acetate was 100%. Other examples are summarized in Table I. In Examples 2–8 of Table I, the catalyst was always dicobalt octacarboxyl at a quantity of 1 mmole. The amount of allyl acetate charged was always 10.0 g and the allyl acetate conversion was always 100%.

TABLE I
HYDROFORMYLATION OF ALLYL ACETATE VIA LOW-PRESSURE COBALT CATALYSTS

| Example No. | Promoter (mmoles) | Solvent | Reaction Conditions | | Selectivity, % | |
|---|---|---|---|---|---|---|
| | | | | | 4-acetoxybutyraldehyde | 2-methyl-3-acetoxypropanal |
| 2 | Ph$_3$GeH (0.25 mmmole) | MIBK (32 g) | CO/H$_2$ = 90° C. 4 Hrs | 1:1 700 psi | 48 | 36 |
| 3 | Ph$_4$Ge (0.5 mmole) | 2-undecanone (32 g) | CO/H$_2$ = 90° C. 4 hrs | 1:2 800 psi | 52 | 11 |
| 4 | Ph$_2$S (2.0 mmmole) | 2-undecanone (35 g) | CO/H$_2$ = 99° C. 6 hrs | 1:2 800 psi | 52 | 15 |
| 5 | Ph$_3$GeH (1.0 mmole) | phenyl ether (35 g) | CO/H$_2$ = 90° C. 6 hrs | 1:2 800 psi | 67 | 16 |
| 6 | Succinonitrile (1.0 mmole) | MIBK (32 g) | CO/H$_2$ = 90° C. 6 hrs | 1:1 800 psi | 61 | 19 |
| 7 | 2,2'-dipyridyl (1.0 mmole) | MIBK (35 g) | CO/H$_2$ = 90° C. 6 hrs | 1:1 750 psi | 66 | 14 |

Many modifications may be made by one skilled in the art without departing from the spirit and scope of the invention which are defined only by the appended claims. For example, the promoter, solvent, proportions and reaction conditions could be changed to optimize the selectivity to 4-acetoxybutyraldehyde.

I claim:

1. A process for preparing 4-acyloxybutyraldehydes which comprises hydroformylating an allylic ester of the formula

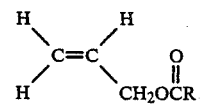

where R is selected form the group consisting of hydrogen and an alkyl radical containing 1 to 6 carbon atoms, by reaction with carbon monoxide and hydrogen in the presence of a cobalt carbonyl compound and a promoter selected from the group consisting of triphenyl germane, tetraphenyl germane, phenyl sulfide and succinonitrile in a polar solvent from the group consisting of methyl isobutyl ketone, 2-undecanone and phenyl ether at a temperature in the range from about 25° C. to 125° C. and at a pressure in the range from about 500 to 1000 psig.

2. The process of claim 1 in which 4-acetoxybutyraldehyde is made by hydroformylating allyl acetate.

3. The process of claim 1 in which the cobalt-containing catalyst is dicobalt octacarbonyl.

4. A process for preparing 4-acetoxybutyraldehyde which comprises hydroformylating allyl acetate by reaction with carbon monoxide and hydrogen in the presence of a dicobalt octacarbonyl catalyst and a promoter selected from the group consisting of triphenyl germane, tetraphenyl germane, phenyl sulfide, and succinonitrile in a polar solvent from the group consisting of methyl isobutyl ketone, 2-undecanone and phenyl ether at a temperature in the range from about 25° C. to 125° C. and at a pressure in the range from about 500 to 1000 psig.

5. The process of claim 4 in which the mole ratio of promoter/catalyst ranges from about 0.1:1.0 to 2.0:1.0.

* * * * *